United States Patent
Ramamurthy et al.

(10) Patent No.: US 6,174,286 B1
(45) Date of Patent: Jan. 16, 2001

(54) MEDICAL DIAGNOSTIC ULTRASOUND METHOD AND SYSTEM FOR ELEMENT SWITCHING

(75) Inventors: Bhaskar S. Ramamurthy, San Jose; Stuart L. Carp, Menlo Park; Albert Gee, Los Altos, all of CA (US)

(73) Assignee: Acuson Corporation, Mountain View, CA (US)

(*) Notice: Under 35 U.S.C. 154(b), the term of this patent shall be extended for 0 days.

(21) Appl. No.: 09/200,663

(22) Filed: Nov. 25, 1998

(51) Int. Cl.[7] .................................................... A61B 8/00
(52) U.S. Cl. ............................................................ 600/447
(58) Field of Search .................................... 600/443, 447; 73/625–626; 361/103, 105

(56) References Cited

U.S. PATENT DOCUMENTS

| | | |
|---|---|---|
| 3,938,502 | 2/1976 | Bom . |
| 4,180,792 | 12/1979 | Lederman et al. . |
| 4,917,097 | 4/1990 | Proudian et al. . |
| 5,285,788 | 2/1994 | Arenson et al. . |
| 5,297,553 | 3/1994 | Sliwa, Jr. et al. . |
| 5,329,930 | 7/1994 | Thomas, III et al. . |
| 5,345,940 | 9/1994 | Seward et al. . |
| 5,456,257 | 10/1995 | Johnson et al. . |
| 5,549,111 | 8/1996 | Wright et al. . |
| 5,551,433 | 9/1996 | Wright et al. . |
| 5,555,534 | 9/1996 | Maslak et al. . |
| 5,563,346 | 10/1996 | Bartelt et al. . |
| 5,570,691 | 11/1996 | Wright et al. . |
| 5,577,505 | 11/1996 | Brock-Fisher et al. . |
| 5,581,517 | 12/1996 | Gee et al. . |
| 5,617,862 | 4/1997 | Cole et al. . |
| 5,623,928 | 4/1997 | Wright et al. . |
| 5,632,277 | 5/1997 | Chapman et al. . |
| 5,667,373 | 9/1997 | Wright et al. . |
| 5,699,805 | 12/1997 | Seward et al. . |
| 5,713,363 | 2/1998 | Seward et al. . |
| 5,740,808 | 4/1998 | Panescu et al. . |
| 5,793,701 | 8/1998 | Wright et al. . |
| 5,795,299 | 8/1998 | Eaton et al. . |
| 5,797,848 | 8/1998 | Marian et al. . |
| 5,808,962 | 9/1998 | Steinberg et al. . |
| 5,823,962 | 10/1998 | Schaetzle et al. . |
| 5,833,613 | 11/1998 | Averkiou et al. . |
| 5,846,205 | 12/1998 | Curley et al. . |
| 5,902,241 | * 5/1999 | Seyed-Bolorforosh et al. ..... 600/443 |
| 5,906,580 | * 5/1999 | Kline-Schoder et al. ........... 600/459 |
| 5,938,612 | * 8/1999 | Kline-Schoder et al. ........... 600/459 |
| 6,014,897 | * 1/2000 | Mo ......................................... 73/628 |

FOREIGN PATENT DOCUMENTS 0 770 352 A1   5/1997   (EP) .

OTHER PUBLICATIONS

Richard E. Kerber, MD, *Coronary Risk Areas: Measurements by Intracardiac Echo and Ultrasound Contrast*, Sep., 1998, p. 8.

James B. Seward et al, *Mayo Clinic Proceedings Ultrasound Cardioscopy: Embarking on New Journey*, Jul., 1996, vol. 71, No. 7, pp. 629–635;.

* cited by examiner

*Primary Examiner*—Francis J. Jaworski
(74) *Attorney, Agent, or Firm*—Craig A. Summerfield, Esq.; Brinks Hofer Gilson & Lione

(57) ABSTRACT

A method and system for obtaining ultrasound data is provided. Two or more transducer elements are shorted or connected to the same transmit or receive channel for a single transmit or receive event. The affect of any grating lobes generated from shorting the transducer elements are minimized by receiving acoustic energy and then obtaining ultrasound data at a harmonic of a fundamental transmit frequency. No contrast agent is added during imaging. A multiplexer with a limited number of switches is used to short pairs of transducer elements together. Alternatively, a multiplexer with a limited number of switches is used to transmit or receive from spaced apertures, such as by connecting a channel to every second transducer element.

56 Claims, 7 Drawing Sheets

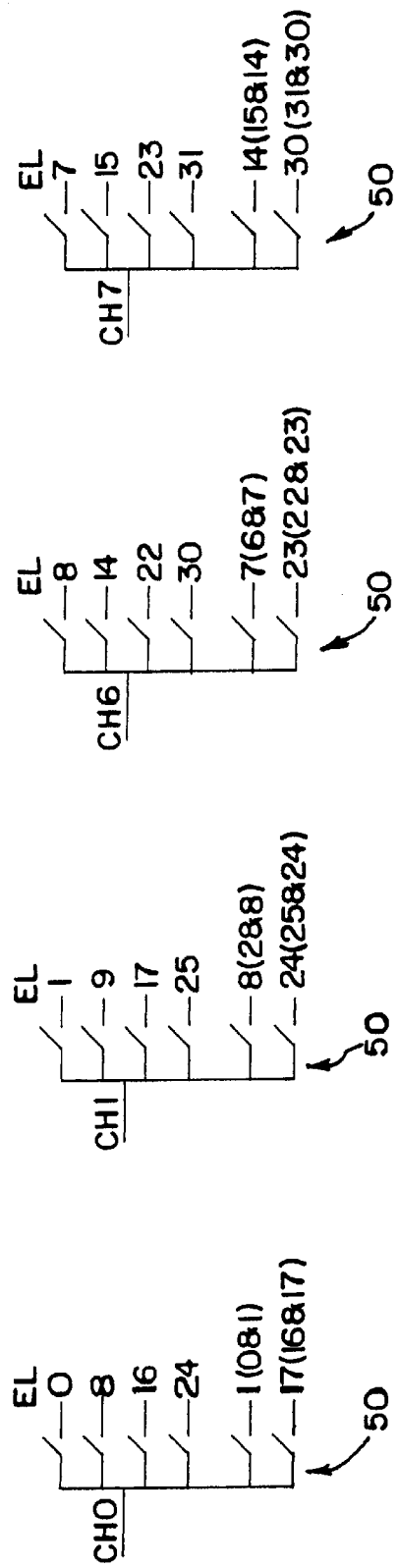

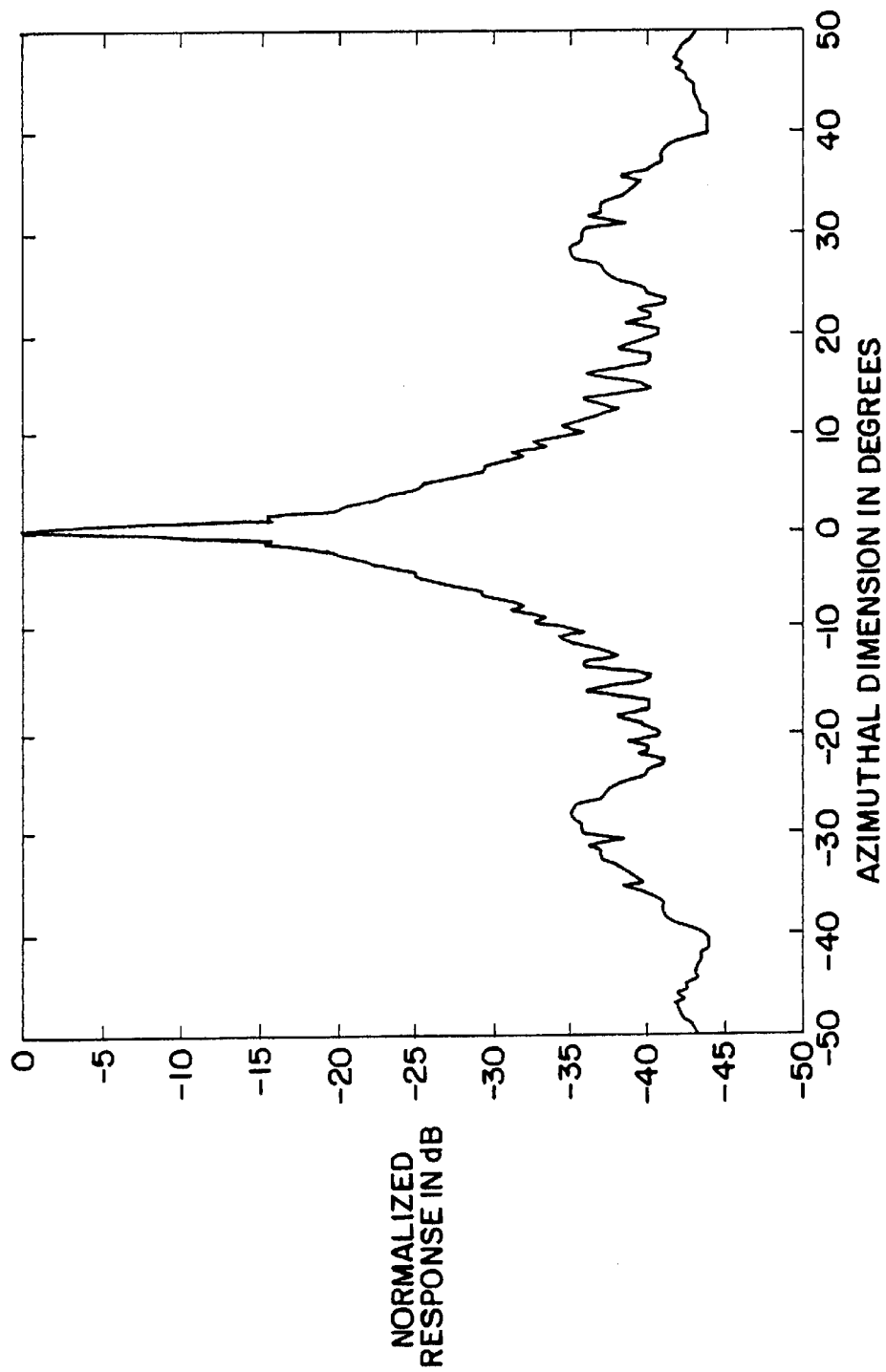

MEDICAL DIAGNOSTIC ULTRASOUND METHOD AND SYSTEM FOR ELEMENT SWITCHING

BACKGROUND

This invention relates to an ultrasound system and method for obtaining ultrasound data using transducer element switching. In particular, switching is used to space apart or short elements together for at least one transmission or reception of acoustic energy, and the resulting reflected echo signals are processed to obtain ultrasound data.

Ultrasound systems generally include transmitters (transmit channels), receivers, processors to control image formation and display monitors. Power supplies drive the transmitters, and control circuitry controls the ultrasound system. The transmitter provides electrical excitation waveforms to a transducer. The electric excitation waveforms are converted to acoustic energy by the transducer for imaging a target. The transducer generally includes a plurality of transducer elements which may be individually excited by respective plurality of transmitters, so each transmitter is connected to one element at any given time.

In a system providing a variable aperture, each one of a plurality of transmit channels may be connected to any one of several transducer elements using a multiplexer. One example of such a variable aperture multiplexer structure is disclosed by Cole et al. in U.S. Pat. No. 5,617,862.

The variable aperture multiplexer structure may be modified to allow a transmit channel to connect to more than one element at a time. As disclosed by Cole et al., switching means and programmability to support adjacent element shorting is provided. In order to connect one transmitter to two or more transducer elements, a multiplexer module in addition to a standard configuration is provided. In one example, the adjacent element shorting structure is used for a transducer with λ/4-spacing of transducer elements. Cole et al. further describes connecting inner and outer elements for simultaneous transmit and receive (a type of multiplexer shorting). With reference to inner and outer active elements, filters for use in second harmonic imaging are disclosed at column 14, lines 5 through 25.

BRIEF SUMMARY

The present invention is defined by the following claims, and nothing in this section should be taken as a limitation on those claims. By way of introduction, the preferred embodiments described below include a method and system for obtaining ultrasound data. In one embodiment, two or more transducer elements are shorted or connected to the same transmit channel for a single transmit event. The effect of any grating lobes generated from shorting the transducer elements during a transmit event are minimized by isolating information at a harmonic of a fundamental transmit frequency. In another embodiment, a multiplexer with a limited number of switches is used to short pairs of transducer elements together. In yet another embodiment, a multiplexer with a limited number of switches is used to transmit from spaced apertures, such as by connecting a transmit channel to every second transducer element.

In a first aspect of one embodiment, a method for obtaining ultrasound data during an imaging session with an ultrasound system is provided. At least two transducer elements are electrically connected to a single transmit channel. The single transmit channel generates an excitation waveform at a fundamental frequency, and, in response, the at least two transducer elements transmit ultrasonic acoustic energy into a target during the imaging session. The target is free of ultrasound contrast agent throughout the entire imaging session. In response to the transmission of ultrasonic energy, ultrasonic data is obtained at a harmonic of the fundamental frequency.

In a second aspect, a system for obtaining ultrasound data is provided. The system includes a transmit beamformer with at least two transmit channels and a transducer with at least four transducer elements. A multiplexer operatively connects one of the two transmit channels to two of the transducer elements during a transmit event. The multiplexer includes less than eight switches for each set of two transmit channels and four transducer elements performing the connections.

In a third aspect, an ultrasonic system for obtaining ultrasonic data is provided. The ultrasound system includes a transmit beamformer with a plurality, P, of transmit channels, M, where M represents transmit channels 0 through P−1. A transducer with at least 2P transducer elements is also provided. A multiplexer is used for operatively connecting each one of the transmit channels M to the transducer elements numbered M and at least M+P, and to at least another transducer elements selected from the group of: transducer elements numbered M+1 and M+P−1. The multiplexer includes less than 4P switches.

Further aspects and advantages of the invention are discussed below in conjunction with the preferred embodiments.

BRIEF DESCRIPTION OF SEVERAL VIEWS OF THE DRAWINGS

FIGS. 4A–D are representations of various switchable apertures for use with the multiplexer structure of FIG. 3.

FIG. 5 is an electrical schematic representation of the multiplexer connections between transmit channels and transducer elements for FIG. 3.

FIGS. 6A and 6B are graphical representations of one-way transmit beamplots.

DETAILED DESCRIPTION OF THE INVENTION

In one preferred embodiment described below, at least one transmit or receive channel is connected to more than one transducer element for a transmit or receive event. For example, adjacent transducer elements are shorted together by a multiplexer. By shorting together transducer elements, a wider aperture using fewer channels may be obtained, tending to decrease the cost of a transmitter or receiver sub-system of the ultrasound system. Shorting adjacent transducer elements together may result in the generation of grating lobes along the azimuthal dimension. The effect of the grating lobes may be minimized by receiving ultrasound data and then obtaining ultrasound information associated with a harmonic of a fundamental transmit frequency.

Figure 1:
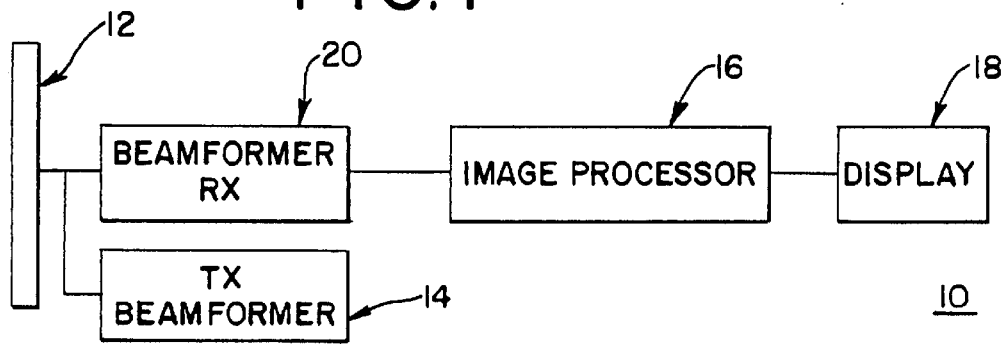
FIG. 1 is a block diagram of an ultrasound system for obtaining ultrasonic data and generating an ultrasound image.

Referring to FIG. 1, an ultrasound system for obtaining ultrasonic data and generating an image is shown at 10. The ultrasound system 10 includes a transducer 12, a transmit beamformer 14, a receive beamformer 20, an image processor 16, and a display 18. Other systems, such as systems with additional or different components, may be used. The various elements of FIG. 1 may be formed in any suitable manner, including a wide variety of conventional systems altered to operate as described below. The widest variety of beamformers, transducers, image processors and displays may be adapted for use with this invention. Both analog and digital beamformer systems are suitable. By way of example, without intending any limitation, the ultrasound imaging systems marketed by Acuson Corporation under the trade name Sequoia®, Aspen™ and 128XP® are capable of being modified to implement this invention. The Sequoia ultrasound imaging system is described, for example, in the following patents: U.S. Pat. Nos. 5,549,111, 5,551,433, 5,555,534, 5,570,691, 5,581,517, and 5,617,862.

The transmit beamformer 14 includes a structure for generating a plurality of transmit waveforms. For example, the transmit beamformer 14 includes programmable waveform generators connected to digital to analog converters. Programmed digital waveforms are converted to analog signals. The analog signals are output to transmit amplifiers to generate excitation waveforms. Other analog or digital transmit beamformers may be used, including non-programmable waveform generators. The shape of the excitation waveforms is determined by the digital output from the programmable waveform generator. Preferably, the excitation waveforms comprise sinusoidal waves at a fundamental frequency modulated by a Gaussian envelope. Other excitation waveforms, such as unipolar or bipolar square or sinusoidal waves, may be used without any, with rectangular or with other shaped modulations.

The transmit beamformer 14 includes a plurality of transmit channels. For example, 32, 64, 128, or 256 transmit channels are provided. Each transmit channel is capable of generating an excitation waveform as discussed above. For example, each transmit channel includes a programmable waveform generator, a digital to analog converter, and a transmit amplifier. In other embodiments, various components are shared by a plurality of transmit channels.

The transducer 12 operatively connects to the transmit beamformer 14 and comprises an array of transducer elements. Each transducer element is substantially separated electrically and acoustically from other transducer elements. Any one or more of various transducers may be used, such as one dimensional linear or curved linear phased arrays. In other embodiments, the transducer 12 comprises a 1.5 dimensional or two-dimensional transducer array. The transducer 12 may comprise any number of transducer elements, such as 32, 64, 128, or 256. Other numbers of transducer elements may be used and may match, but preferably exceed the number of transmit channels.

Preferably, the transducer elements are spaced as a function of the wavelength associated with the highest operating frequency (transmit or receive frequency), such as the fundamental or a harmonic of the fundamental. For steered arrays, the transducer elements are preferably spaced by about ½ the wavelength of the highest operating frequency. In alternative embodiments, the spacing is about a quarter of a wavelength or 1 to 2 wavelengths. For a non-steered arrays, the spacing is about 1 wavelength of the receive frequency, but may be ½ or 2 to 4 wavelengths. Other spacings may be used.

The spacing is measured from the center of the transducer element to the center of another transducer element. The spacing of the adjacent transducer elements is said to be "about" a function of the wavelength of the receive frequency to account for manufacture tolerances, changes in transmit or receive frequencies within the transducer bandwidth, and other design choices.

The excitation waveforms from the transmit channels of the transmit beamformer 14 are provided to a respective plurality of transducer elements. In response to the excitation waveforms, the transducer elements generate acoustical energy. The acoustical energy is focused along one or more ultrasound scan lines as a function of various delays and apodizations relative to each excitation waveform. By varying the relative delays, acoustic energy may be sequentially or simultaneously generated along different scan lines. Any of various scan formats may be used, such as linear, curved linear, Vector®, sector, or other formats. The scan region may be responsive to a single possible aperture, such as transmitting from all or a subset of all the transducer elements for each transmit event. In alternative embodiments, a sliding or variable aperture associated with transmitting from different subsets of transducer elements for different transmit events may be used. As used herein, a single transmit event comprises transmitting excitation waveforms along one or more scan lines substantially simultaneously.

In one embodiment, the number of transmit channels equals the number of transducer elements. Alternatively, there are more or less transmit channels than transducer elements. Various of the embodiments described below may use all or only a sub-set of either or both the transmit channels or transducer elements.

Figure 2:
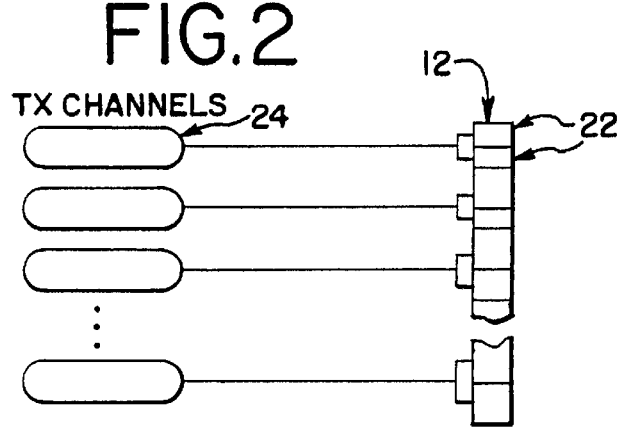
FIG. 2 is a graphical representation of connection between a plurality of transmit channels and a plurality of shorted transducer elements.

The number of transmit channels for use with any given aperture or set of transducer elements may be reduced by shorting two or more transducer elements together. Referring to FIG. 2, a representation of shorting pairs of adjacent transducer elements 22 to each transmit channel 24 is shown. Each pair of adjacent elements 22 are shorted to a single transmit channel 24, effectively forming one large element for beamformer purposes. The two elements 22 shorted together are excited at the same time by the same waveform generated by the transmit channel 24. Fewer transmit channels 24 may be used to obtain a same aperture width and an associated beamwidth as provided by twice the number of transmit channels 24. Other sets of elements 22 may be shorted together, such as shorting elements 22 separated by one or more additional elements, shorting inner and outer elements together and other configurations. More than two elements may be shorted together.

The elements 22 are shorted together by electrically connecting the elements 22. The electrical connection may be made using any of various techniques, such as connected with an electrical trace, switching structures, other circuitry, or multiplexer structures as discussed below.

Figure 6A:
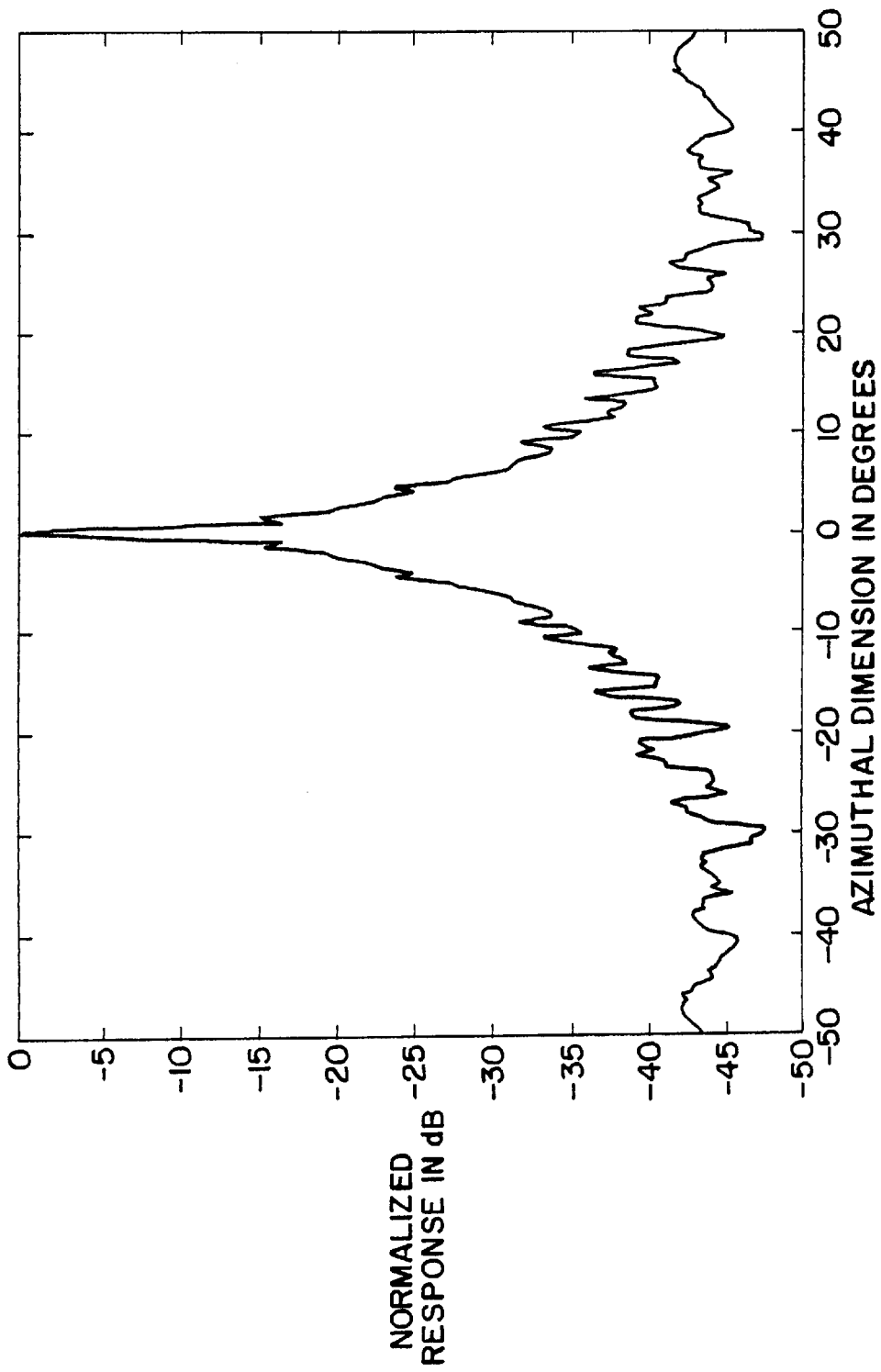

Referring to FIGS. 6A and 6B, one-way transmit beam plots using 64 separate single elements and adjacent element shorting of the 64 elements, respectively, are shown. In FIG. 6A, a 5 MHz transmit frequency with a 19 mm aperture using a 64 independently excited transducer elements is shown. The resolution is 2 mm at −6 dB. FIG. 6B shows a beam plot generated using the same aperture and 64 elements with half the number of transmit channels and adjacent element shorting at the 5 MHz fundamental transmit frequency. As is shown by a comparison of FIGS. 6A and 6B, the beamwidth and associated azimuthal resolution is similar.

If two or more elements 22 are shorted together, the power associated with the excitation waveform generated by the transmit channel 24 is preferably increased. In one embodiment, the current output by each transmit channel is doubled for shorting two elements 22 together. Where possible, the current output is changed, such as changing the amplitude output from the programmable waveform generator. Alternatively, an output gain stage is designed to have increased output power for the same or a different excitation signal. The power supply driving the transmit channel is also changed to provide the increased power. The output current of the transmitter channel 24, when connected to two transducer elements 22 in parallel, may be doubled without exceeding any limits on the acoustic power when compared to using two transmit channels 24 connected to respective two transducer elements 22. The peak to peak output voltage swing of the excitation waveform is a function of the output current of the transmit channel 24 and the load impedance of the transducer elements 22. Shorting together adjacent transducer elements 22 cuts the load impedance in half. Therefore, twice as much current may be output by the transmit channel for a pair of shorted elements than for a pair of transmit channels 22 connected to a respective pair of transducer elements 22, without exceeding the breakdown voltage. Each of the shorted transducer elements 22 will conduct half the total current output by the transmit channel 24. Therefore, a single transmit channel 24 may drive two transducer elements 22 to generate substantially the same acoustic signal power as two transmit channels separately driving the same two transducer elements.

Since it is often more practical to design the transmit channel 24 with a high output current capability than a high output voltage capability, shorting the elements 22 together and driving them from a single high current output transmit channel 24 is a cost effective method to increase transmitted acoustic power.

Increasing the power of the excitation waveforms output by the transmit channels 24 to the shorted transducer elements 22 provides a substantially similar acoustic output power generated by twice the number of transmit channels 24 connected to non-shorted transducer elements 22. By reducing the number of transmit channels 24, the cost of the associated transmit beamformer 14 (FIG. 1) may be reduced. In alternative embodiments, the number of transmit channels 24 and/or the output of the power supply and each associated transmit channel 24 is increased to increase the transmit acoustic power. Preferably, the power associated with the excitation waveform does not exceed the breakdown voltage of any of the components within the transmit channel 24, such as capacitors, resistors, and transistors.

The transmitted acoustic energy propagates through the target, and some of the acoustic energy is reflected back towards the transducer 12. Using the same or different transducer elements 22, the reflected acoustic energy is converted into received electrical signals.

The received electrical signals are provided to the receive beamformer 20. The receive beamformer 20 preferably includes a plurality of receive channels. In one embodiment, each receive channel includes an amplifier for amplifying the received electrical signals. The amplified signals are digitized and delayed for each receive channel relative to the other receive channels. The delayed signals are summed together to form a coherent signal. Other receive beamformers and associated receive channels may be used, such as analog receive beamformer systems.

Each receive channel may be associated with one or more transducer elements 22. For example, no shorting of transducer elements is provided for receiving reflected acoustic energy. In alternative embodiments, the same or different groupings or shorting of the elements 22 is used for reception as is for transmission of acoustic energy.

The coherent signal is filtered to obtain ultrasound data at a desired frequency, such as the fundamental or a harmonic frequency. As used herein, a fundamental or harmonic frequency includes a band of frequencies centered around the particular fundamental or harmonic frequency. Also as used herein, harmonic is intended broadly to include any one of various higher harmonics (e.g., two or three times the fundamental frequency at which the transmit beam is centered). For example, a band pass filter is used to obtain information at a second harmonic frequency. Filtering may also be implemented using demodulation to a baseband frequency, such as 0 Hz, and low pass or bandpass filtering to isolate information at or near the baseband frequency. The filtered signals may be processed to generate an analytical lines with synthetic line interpolation as discussed in U.S. Pat. Nos. 5,623,928, 5,667,373 and 5,793,701.

In one preferred embodiment, the coherent signals are filtered to obtain information associated with a harmonic frequency of the fundamental transmit frequency, such as the second harmonic. A filter may be used in the receive beamformer or at other locations in the ultrasound system. Through non-linear propagation, harmonics of the fundamental transmit frequency are generated. Images may be formed from information generated by these non-linear processes. These images display increased resolution and decreased clutter. Imaging using harmonic information may also minimize artifacts generated by grating lobes generated from transmitting from shorted or spaced elements.

The harmonic imaging techniques described above can be used for both tissue and contrast agent harmonic imaging. In harmonic imaging of tissue, no additional contrast agent is added to the target, and only the non-linear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the entire imaging session.

In contrast agent harmonic imaging, any one of a number of known ultrasound contrast agents generating increased non-linear response, such as microspheres or the FS069 agent by Schering of Germany, is added to the target or subject in order to enhance the non-linear response of fluid. The contrast agents radiate ultrasonic energy harmonics of an insonifying energy at fundamental frequencies.

The ultrasound data, either at a harmonic or fundamental frequency, is output by the receive beamformer 20 to the image processor 16. The image processor includes a B-mode and/or a Doppler processor. For B-mode processing, the signals are detected and logarithmically compressed. For Doppler processing, an estimate of the velocity of a target is generated. In addition to velocity estimates, acceleration and energy estimates may also be generated. The Doppler processor may also generate spectral Doppler strip information. The output data of the B-mode and/or Doppler processors is provided to a scan converter. The scan converter converts the polar coordinate output data to cartesian coordinate data for display on a monitor. The display includes one of or a combination of B-mode and Doppler information.

Shorting adjacent elements 22 and using harmonic receive processing may be used to acquire information representing the motion of tissue, such as using Doppler techniques as disclosed in U.S. Pat. No. 5,285,788. the disclosure of which is incorporated herein by reference.

In one preferred embodiment, a switching structure is used to allow for a variable aperture. In this embodiment, different transducer elements may be shorted together or spaced transducer elements may be used for generating acoustical energy with fewer transmit channels or receiving acoustical energy with fewer receive channels.

Figure 3:
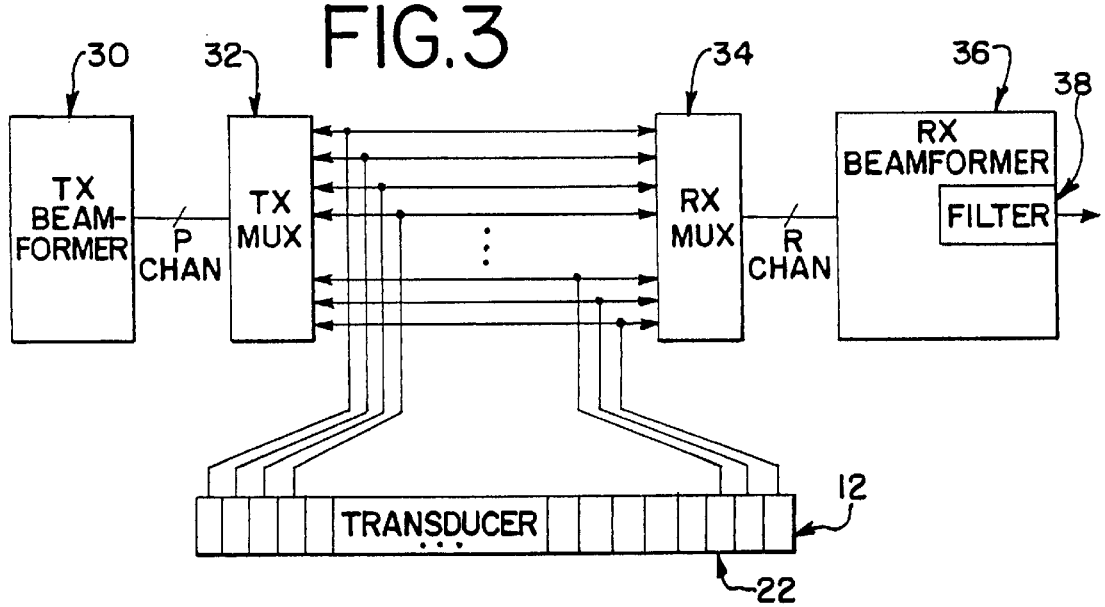
FIG. 3 is a block diagram representation of a multiplexer structure for performing the shorting as represented by FIG. 2.

Referring to FIG. 3, a schematic block diagram of a transmit and receive structure for using a variable aperture is shown. A transmit beamformer 30 connects to a transmit multiplexer 32. Preferably, the transmit multiplexer comprises high voltage FET switches. A receive multiplexer 34 connects to a receive beamformer 36. Preferably, the receive multiplexer 34 comprises high voltage diode switches, such as disclosed in U.S. Pat. No. 5,617,862. The receive beamformer 36 includes a filter 38. The transducer 12 and the associated array of elements 22 are each independently electrically connectable to both the transmit beamformers 30 and the receive beamformer 36. A plurality, P, of transmit channels, M, within the transmit beamformer 30 connect to the transmit multiplexer 32. Likewise a plurality, R, of receive channels of the receive beamformer 36 are connected to the receive multiplexer 34. P may equal R, but more or fewer transmit or receive channels may be used. In one embodiment, the transmit and receive structure of FIG. 3 comprises the variable aperture system disclosed in U.S. Pat. No. 5,617,862, the disclosure of which is incorporated herein by reference. Other multiplexer or switching networks may be used.

Using the transmit multiplexer 32, the P transmit channels or a subset of the P transmit channels may be operatively connected to different elements 22 of the transducer 12. By switching which elements 22 are connected to the P or a subset of the P transmit channels, the aperture used may be varied. For example, P=64 transmit channels for connection with various ones of a 128 elements 22. The 64 transmit channels may be operatively connected through the transmit multiplexer 32 to different groupings of the transducer elements 22 for different transmit events. In one embodiment for imaging with a synthetic aperture, the 64 transmit channels are connected to the leftmost transducer elements 22. Excitation waveforms with appropriate delays are used to generate acoustical energy focused at an area within the target. After reflected acoustic energy is received along a portion or the entire range of interest of the scan line, the transmit multiplexer 32 operatively connects the 64 transmit channels to the right most transducer elements 22. The focus and delay profiles of the excitation waveforms are altered in order to image the same area of the target as was imaged with the excitation waveforms of the left half of the transducer 12. Receive signals associated with the scan lines generated by the left half and the right half of the transducer 12 are combined to generate a composite scan line. This process is disclosed in U.S. Pat. Nos. 5,623,928, 5,667,373 and 5,793,701, the disclosures of which is herein incorporated by reference. This process is repeated in order to scan a plurality of focal areas within a region of the target. In alternative embodiments, the synthetic aperture comprising all the elements 22 of the transducer 12 is used in different ways than the right half and left half division, such as using every odd transducer element 22 and then every even transducer element 22, using inner and outer subsets of transducer elements 22 or other divisions. Other receive aperture configurations are possible, including using the same configurations and associated switching as the transmit aperture configurations discussed herein.

Using the variable aperture to generate composite information as discussed above may be used where elements 22 are shorted together. For example, 32 transmit channels may be connected to 64 transducer elements 22. Preferably, adjacent elements 22 are shorted together by switching a single transmit channel in the transmit multiplexer 32 to two adjacent transducer elements 22. In alternative embodiments, the 32 transmit channels are connected to every other transducer element without any shorting. Connecting the transmit channels to every other element or shorting adjacent pairs of elements effectively makes the elements more spaced, creating grating lobes. The receive aperture configuration may be the same or different than the transmit aperture configuration. To minimize the effect of grating lobes, the receive beamformer 36 and the filter 38 obtains and isolates ultrasound data associated with a harmonic of the fundamental transmit frequency. The various aperture combinations discussed above may be used in this embodiment.

Figure 7:
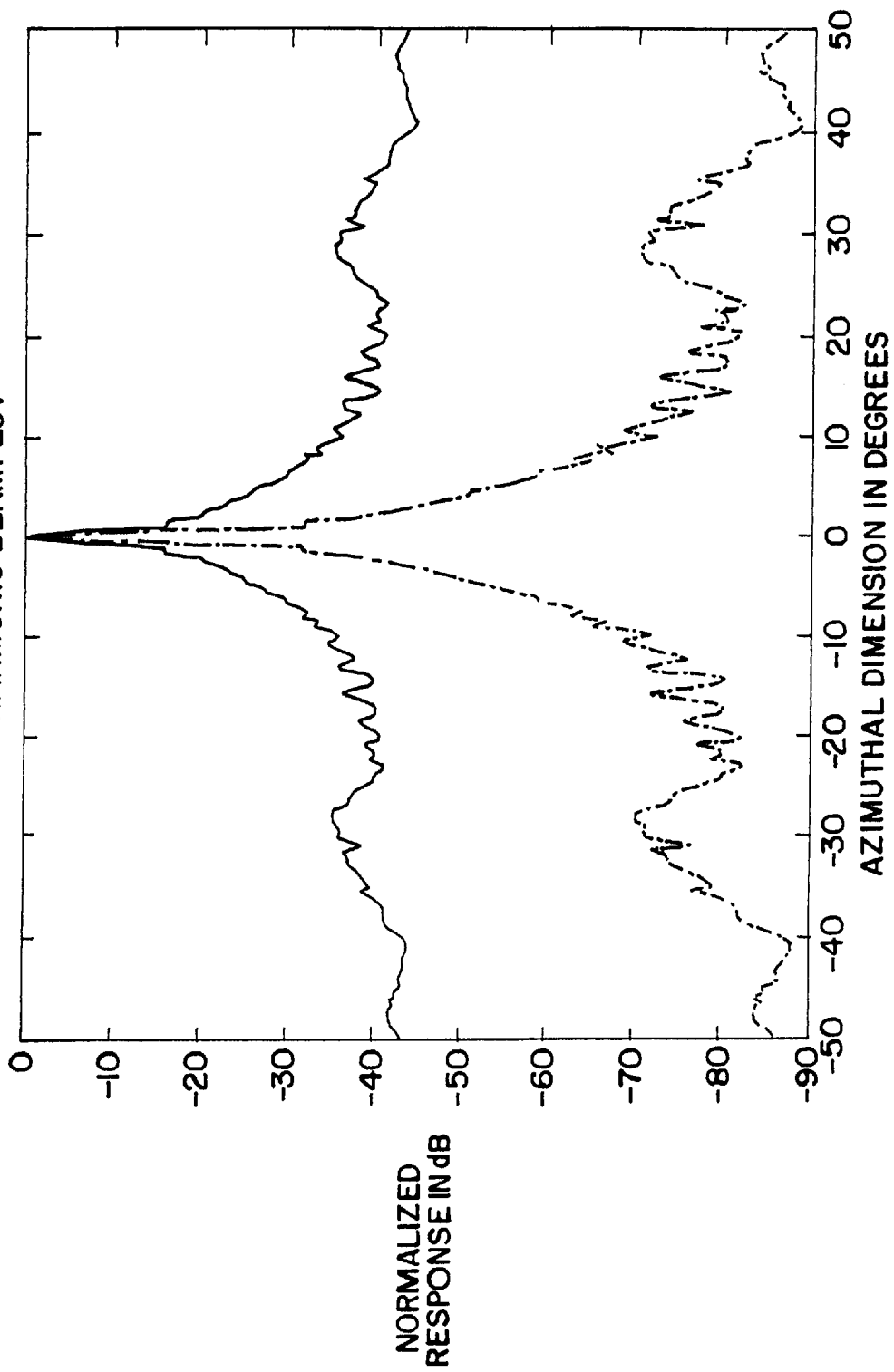
FIG. 7 is a graphical representation of a two-way transmit and receive beamplot using a left-right grouping of transducer elements.

Referring to FIG. 7, the one-way azimuthal response associated with transmission by 32 transmit channels connected to 64 adjacent elements 22 is shown. The solid line represents the one-way response at the fundamental transmit frequency with adjacent element shorting. The dashed line represents the one-way response at the second harmonic of the fundamental frequency.

In one embodiment, left-right synthesis or combination of apertures is provided. In alternative embodiments, the inner 64 elements 22 comprise one aperture and two subsets of 16 outer elements 22 comprises a second aperture. Other aperture configurations for generating synthetic scan line data may be used.

In alternative embodiments, the transmit multiplexer 32 and/or the receive multiplexer 34 are used to generate a sliding variable aperture. A subset of the total number of elements 22 is operatively connected to the transmit channels 24. After one or more transmit events, the aperture is adjusted or slid to different elements 22. For example, the transmit multiplexer 32 slides the aperture in steps of one or more transducer elements (i.e. transducer elements 0 through 7 are connected for one transmit event and transducer elements 1 through 8 are connected for a second transmit event). More or fewer transducer elements and transmit channels may be used.

Figures 4A, 4B, 4C, 4D:
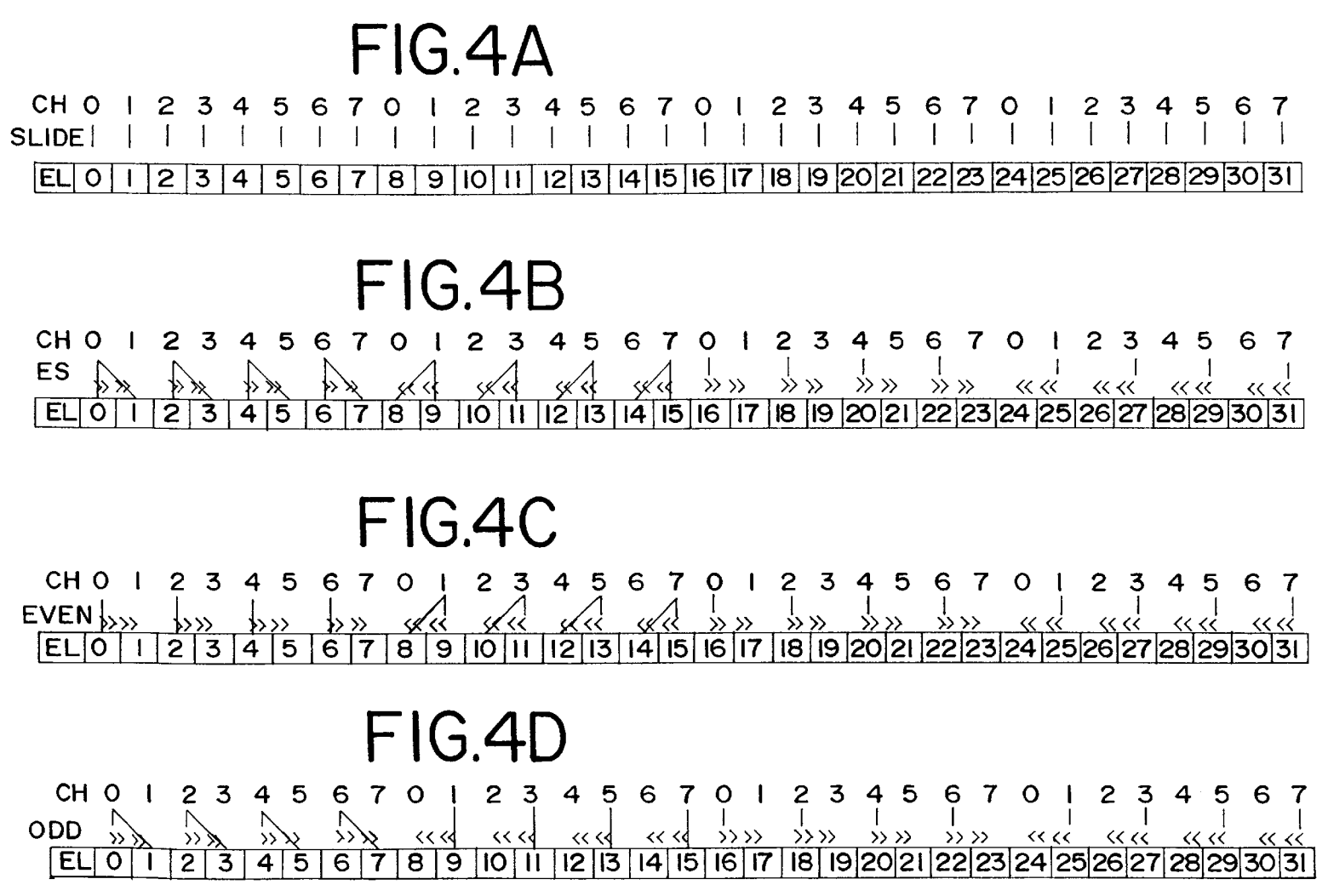

Referring to FIG. 5, an electrical schematic for implementing the transmit multiplexer 32 and/or the receive multiplexer 34 to connect the transmit or receive channels and associated transducer elements shown in FIGS. 4A and B is shown. The transmit or receive multiplexers 32 or 34 comprise a single layer of multiplexers or switching networks 50. One multiplexer 50 is provided for each channel. Given P transmit channels 24, each transmit channel numbered M (0 through P−1) is connectable through the multiplexer 50 to a transducer element of the same number M, element number P+M, element number 2×P+M, element number 3×P+M . . . . This structure provides for a sliding aperture. The number of transducer elements 22 is preferably a multiple of the number of transmit channels P, such as 2P, 3P, 4P , . . . . If the number of transducer elements is 2P and the number of transmit channels is P or fewer, 2P switches are required to ensure that each transducer element 22 may be connected to a transmit channel.

In one embodiment represented by FIG. 4A, 8 transmit channels, labeled channel 0 through channel 7, are provided for switchable connection to 32 transducer elements, labeled element 0 through element 31. A sliding aperture of 8 elements using all the elements 0 through 31 may be defined by 32 switches. In this embodiment, transmit channel 0 is connectable to element 0, element 8, element 16 and element 24. Likewise channel 1 is connectable to element 1, element 9, element 17, and element 25. This pattern continues for the remaining transmit channels. One aperture is defined by connecting channels 0 through 7 to respective elements 0 through 7. To vary the aperture or slide the aperture by one element, channel 0 is connected to channel 8. The remaining channels 1 through 7 are still connected to the respective elements 1 through 7. The aperture is moved one step to the right. Preferably, the transmit beamformer 30 and the associated transmit channels 24 account for the various switching connections to provide the appropriate delay and apodized excitation waveforms to the connected transducer elements. The waveform may vary from element to element.

To provide for adjacent element shorting, shorting of two or more elements together or transmission or reception from spaced elements, such as even or odd numbered elements, additional switches are provided on each multiplexer 50. For even numbered transmit channels M (e.g. 0, 2, 4 . . . ), these additional switches are provided to connect the channel M to transducer elements M+1, 2×P+M+1, 4×P+M+1 . . . For each odd numbered transmit channel M, electrical switches for connection to the transducer elements P+M−1, 3×P+M−1, 5×P+−1 . . . are provided as shown in FIG. 5. In the example represented in FIGS. 4 and 5, channel 0 may be additionally connectable to elements 1 and 17. Channel 1 is additionally connectable to elements 8 and 24. The pattern continues through channel 7 as shown, which is connectable to additional elements 14 and 30. Other patterns may be used, such as connecting Channel 1 to elements 1 and 0, Channel 3 and elements 3 and 2, and so on (i.e. reverses the connections discussed above).

These additional switches within the multiplexers 50 allow for various aperture configurations. For example adjacent element shorting is provided as shown in FIG. 4B. Each transmit channel M is connected to two adjacent transducer elements. Transducer elements 0 and 1 are connected to transmit channel 0, transducer elements 2 and 3 are connected to transmit channel 2, and so on as shown. Using the multiplexers 50 shown in FIGS. 4B and 5, fewer switches than 2 times the number of transducer elements designate an aperture. Fewer switches may provide a more efficient implementation. In particular, a number of switches that is only 1.5 times the total number of transducer elements are operable to designate an aperture of adjacent shorted elements which can slide across the array. To slide the aperture, channel 0 is connected to elements 16 and 17. Steps associated with a greater number of transducer elements may be used. The aperture for adjacent shorted elements is 16 elements wide using only 8 transmit or receive channels.

Using the same multiplexers 50 shown in FIG. 5, various other apertures may be used for transmission or reception. For example, the 8 transmit channels may be connected to even transducer elements as shown in FIG. 4C, or to odd transducer elements as shown in FIG. 4D. These connections comprise a subset of the connections shown in FIG. 4B. Likewise and as shown in FIG. 4D the aperture defined by odd numbered transducer elements is a subset of the aperture shown in FIG. 4B. These even or odd transducer element array apertures may also be slid across the full transducer array. Preferably, harmonic receive processing is also used for the apertures shown in FIGS. 4C and 4D. In alternative embodiments, the multiplexers 50 of FIG. 5 are used to designate a single arbitrary aperture for all transmit and/or receive events (i.e. non-sliding), an aperture for any of the combinations discussed above, or any other moving or non-moving aperture, including any sub-set or all of the transducer elements.

By providing the various aperture configurations as discussed above with the multiplexers 50, each excitation waveform only passes through one switch between the transmit channel and the transducer element. Likewise, the received signal only passes through one switch between the receive channel and the transducer element. Therefore, alterations to the excitation waveforms or receive signals caused by switching structures and timing adjustments associated with a multiple layer switching structure are avoided.

The receive multiplexer 34 of FIG. 3 may comprise the same multiplexer structure as represented in FIGS. 4 and 5. In alternative embodiments, the transmit and receive multiplexers 32 and 34 comprise different structures. In one preferred embodiment, the receive channels of the receive beamformer 36 operatively connect to the same transducer elements as respective transmit channels of the transmit beamformer 30. In alternative embodiments, twice as many receive channels are provided, so that transducer elements 22 are not shorted together or spaced apart for receive processing. In yet other alternative embodiments, fewer receive channels are used, such as shorting adjacent elements 22 to respective receive channels and connecting a greater number of transmit channels to non-shorted and non-spaced transducer elements 22.

Figure 8A:
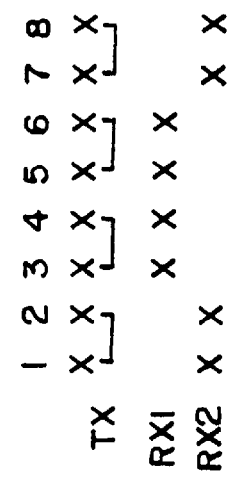
FIGS. 8A–8C are representations of various switchable apertures.
Figure 8B:
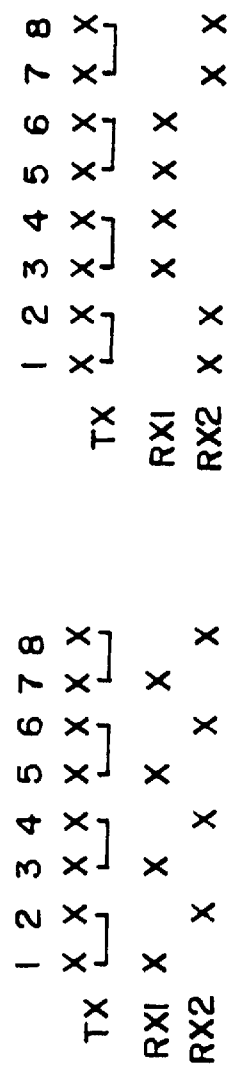
Figure 8C:
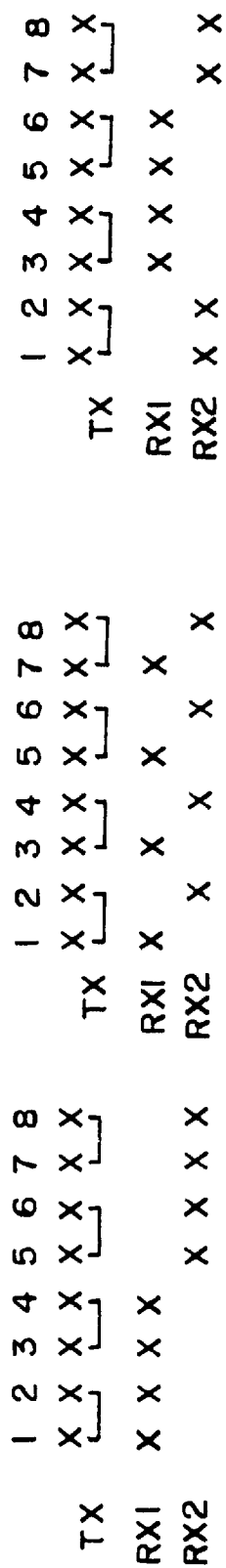

Referring to FIGS. 8A through 8C, various switchable aperture configurations for transmit and receive processing are shown. The aperture configuration for transmit processing is represented by "TX," and the aperture configuration for receive processing is represented by "RX." Shorting as discussed above is represented by a bracket connecting elements "x". The transmit aperture configurations shown may be implemented using 1.5N switches, such as using the multiplexer described above, where N is the number of transducer elements. The receive aperture configuration of FIG. 8B preferably also uses 1.5N switches. The receive aperture configurations of FIGS. 8A and 8C may use 1N switching, such as connecting one channel to one element. More switches may be used for any of the transmit or receive configurations.

Multiple transmit or receive events may be used. For example and referring to FIG. 8A, the acoustic energy is transmitted twice using the configuration represented by TX. For the first transmit event, the receive configuration represented by RX1 is used. For the second transmit event, the receive configuration represented by RX2 is used. Other configurations on transmit or receive, with or without multiple transmit or receive configurations, and with or without element shorting or spacing, may be used. Eight elements are shown for convenience, and the aperture may comprise more or fewer elements.

Figure 9:
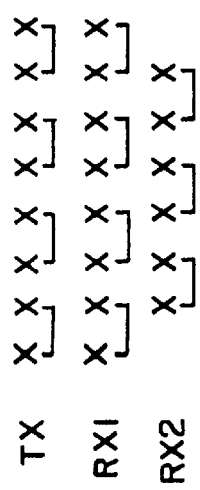
FIG. 9 is a representation of a switchable apertures.

Referring to FIG. 9, an additional switchable apertures is shown using the representations discussed above. The implementations shown in FIG. 9 may require additional switches, such as 2N switches, to implement the receive aperture configuration. For 2N switches, each odd channel is connectable to elements M, M+1, M−1, P+M, P+M−1, P+M+1, 2P+M, 2P+M−1, 2P+M+1 . . . . Each even channel is connectable to elements M, M+1, M−1, P+M, P+M+1, P+M−1, 2P+M, 2P+M−1, 2P+M+1 . . . .

Figure 10:
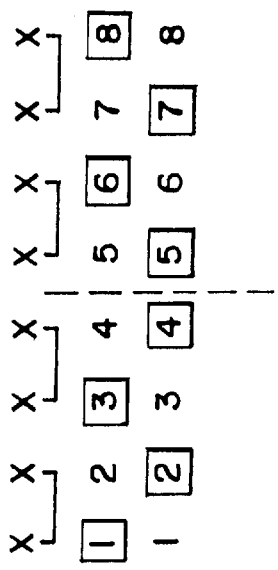
FIG. 10 is a representation of a switchable aperture.

Referring to FIG. 10, an aperture configuration requiring only 1N switches for the receive aperture configuration is shown. Using a 1N switching structure discussed above, elements 1–8 may be connected to respective receive channels 1–4. The receive aperture comprises a mirror image about the center of the aperture, allowing for fewer switches.

Referring to FIGS. 8A–8C, 9 and 10, other combinations of elements with shorting or spacing for transmit and/or receive are possible. These figures represent a few possible combinations.

By providing a multiplexer or other structure for transmitting or receiving from spaced elements or shorted elements, fewer transmit and/or receive channels may be used. By reducing the number of transmit and/or receive channels, the cost of an ultrasound system may be decreased. The grating lobes and associated artifacts resulting from shorting transducer elements together or transmitting from spaced transducer elements may be reduced by using harmonic information for imaging. Furthermore, the multiplexer structure described above may be used for generating any one of various apertures associated with no element shorting.

While the invention has been described above by reference to various embodiments, it will be understood that many changes and modifications can be made without departing from the scope of the invention. For example, different multiplexer structures, including layered multiplexers or switching networks with more or fewer switches, may be used to provide for adjacent element shorting or spaced element transmission or reception. Furthermore, imaging based on information received at the fundamental frequency may be used. Different receive and/or transmit configurations using one or both of element shorting or spacing may be used.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for obtaining ultrasound data during an imaging session with an ultrasound system, the method comprising the steps of:
   (a) electrically connecting at least two transducer elements to a single channel;
   (b) generating an excitation waveform at a fundamental frequency;
   (c) transmitting ultrasonic energy responsive to the excitation waveform into a target during said imaging session, said target being free of ultrasound contrast agent throughout the entire imaging session;
   (d) receiving energy responsive to step (c); and
   (e) obtaining ultrasound data at a harmonic of the fundamental frequency in response to step (d)
   wherein one or both of steps (c) and (d) are performed using the connection of step (a).

2. The method of claim 1 wherein step (a) comprises electrically connecting adjacent pairs of transducer elements of an array of elements.

3. The method of claim 1 wherein step (a) comprises electrically connecting the at least two transducer elements with a multiplexer.

4. The method of claim 3 wherein step (a) comprises connecting the single channel to said at least two transducer elements during a transmit event, the single channel and said at least two transducer elements comprising one of a plurality of sets and the multiplexer comprising three switches for each of a plurality of pairs of said sets.

5. The method of claim 3 further comprising a plurality P of transmit channels M and the at least two transducer elements comprises at least 2P transducer elements numbered 1–2P sequentially from one end of a linear array to another end of the linear array;
   wherein step (a) comprises connecting each one of said transmit channels M to the transducer elements numbered M and at least M+P, and to at least another transducer element selected from the group of: transducer element numbered M+1 and P+M−1, the multiplexer comprising less than 4P switches.

6. The method of claim 1 wherein step (e) comprises obtaining ultrasound data at a second harmonic of the fundamental frequency.

7. The method of claim 1 further comprising (f) providing about double the output power than for one of the at least two transducer elements.

8. The method of claim 1 further comprising:
   (f) electrically connecting at least two additional transducer elements to the single transmit channel;
   (g) generating an additional excitation waveform at the fundamental frequency with the single transmit channel;
   (h) transmitting ultrasonic energy responsive to the additional excitation waveform from the at least two additional transducer elements into the target during said imaging session; and
   (i) obtaining ultrasound data at the harmonic of the fundamental frequency in response to step (h).

9. The method of claim 1 further comprising:
   (f) scanning a region of the target with sliding aperture.

10. The method of claim 1 wherein the single channel comprises a transmit channel and further comprising:
    (f) electrically connecting each of a plurality of receive channels to respective ones of the at least two transducer elements prior to performing step (e).

11. The method of claim 1 further comprising:
    (f) electrically connecting the at least two transducer elements to a single receive channel prior to performing step (e).

12. The method of claim 1 further comprising:
    (f) switching the single channel to two different transducer elements of the at least two transducer elements in a synthetic aperture.

13. The method of claim 1 further comprising:
    (f) acquiring information representing tissue motion of the target from the ultrasound data.

14. An ultrasound system for obtaining ultrasound data during an imaging session, the ultrasound system comprising:
    at least two transducer elements for transmitting ultrasonic energy into a target during said imaging session, said target being free of ultrasound contrast agent throughout the entire imaging session;
    a single transmit channel electrically connected to the at least two transducer elements for generating an excitation waveform at a fundamental frequency;

a receive channel operatively connected to at least one of the at least two transducer elements after transmission of the ultrasonic energy for receiving signals responsive to the excitation waveform; and a beamformer responsive to the receive channel for obtaining ultrasound data from the received signals at a harmonic of the fundamental frequency.

15. The system of claim 14 wherein the at least two transducer elements comprise an adjacent pair of transducer elements of an array of elements.

16. The system of claim 14 further comprises a multiplexer for electrically connecting the at least two transducer elements to the signal transmit channel.

17. The system of claim 16 wherein the multiplexer connects the single transmit channel to said at least two transducer elements during a transmit event, the multiplexer comprising three switches for each of a plurality of sets of two transmit channels and a plurality of sets of four of the at least two transducer elements.

18. The system of claim 16 further comprising a plurality P of transmit channels M, where the single transmit channel comprises one of the plurality P, and the at least two transducer elements comprises at least 2P transducer elements numbered 1–2P sequentially from one end of a linear array to another end of the linear array;

wherein the multiplexer connects each one of said transmit channels M to the transducer elements numbered M and at least M+P, and to at least another transducer element selected from the group of: transducer element numbered M+1 and P+M−1, the multiplexer comprising less than 4P switches.

19. The system of claim 14 wherein the beamformer comprises a filter for obtaining ultrasound data at a second harmonic of the fundamental frequency.

20. The system of claim 14 wherein the single transmit channel comprises a current source operable to double an output power for use with the at least two transducer elements than when connected with a single transducer element.

21. The system of claim 17 wherein the multiplexer is operable to scan a region of the target as a function of a sliding aperture.

22. The system of claim 14 wherein the receive channel electrically connects to a single one of the at least two transducer elements.

23. The system of claim 14 wherein the receive channel electrically connects to the at least two transducer elements.

24. The system of claim 14 wherein the single channel is operably sequentially electrically connectable to a different two transducer elements for use in a synthetic aperture.

25. The system of claim 14 further comprising a Doppler processor for acquiring tissue motion information of the target responsive to the ultrasound data.

26. An ultrasound system for designating an aperture, the system comprising:

a transmit beamformer comprising at least two transmit channels;

a transducer comprising at least four transducer elements; and a multiplexer operable to connect one of said at least two transmit channels to two adjacent elements at an end of the aperture regardless of the end element position during a transmit event, the multiplexer comprising less than eight switches for each set of two transmit channels and of four transducer elements.

27. The system of claim 26 wherein the transmit beamformer is operable to generate excitation waveforms at a fundamental frequency further comprising:

a receive beamformer operatively connected to the transducer; and a filter for obtaining ultrasound data at a harmonic of the fundamental transmit frequency in response to transmissions with the excitation waveform.

28. The system of claim 26 wherein the at least two transmit channels comprise a plurality P of transmit channels M;

the at least four transducer elements comprising at least 2P transducer elements numbered 1–2P sequentially from one end of a linear array to another end of the linear array; and the multiplexer being for operatively connecting each one of said transmit channels M to the transducer elements numbered M and at least M+P, and to at least another transducer element selected from the group of: transducer element numbered M+1 and P+M−1, the multiplexer comprising less than 4P switches.

29. The system of claim 28 wherein the multiplexer comprises 3P switches.

30. The system of claim 27 wherein the transducer transmits acoustic energy into a target during an imaging session, said target being free of ultrasound contrast agent throughout the entire imaging session.

31. The system of claim 26 wherein the transducer comprises 128 elements.

32. The system of claim 26 wherein the multiplexer is operable to short every one of the transducer elements to another one of the transducer elements in an aperture regardless of the aperture position.

33. A method for designating an aperture in an ultrasound system, the method comprising the steps of:

(a) generating excitation waveforms with a transmit beamformer comprising at least two transmit channels;

(b) transmitting acoustic energy responsive to the excitation waveforms from a transducer comprising at least four transducer elements; and (c) connecting one of said at least two transmit channels to two adjacent elements at an end of the aperture regardless of the end element position during a transmit event comprising (a) and (b) with a multiplexer comprising less than eight switches for each set of two transmit channels and of four transducer elements.

34. The method of claim 33 wherein (b) comprises transmitting at a fundamental transmit frequency further comprising:

(d) obtaining ultrasound data at a harmonic of the fundamental transmit frequency.

35. The method of claim 33 wherein:

step (a) comprises generating with a plurality P of transmit channels M;

step (b) comprises transmitting acoustic energy from a sub-set of at least 2P transducer elements; and step (c) comprises connecting each one of said transmit channels M to the transducer elements numbered M and at least M+P, and to at least another transducer element selected from the group of: transducer element numbered M+1 and M−1, the multiplexer comprising less than 4P switches.

36. The method of claim 34 wherein step (b) comprises transmitting the acoustic energy into a target during an imaging session, said target being free of ultrasound contrast agent throughout the entire imaging session.

37. The method of claim 33 wherein step (c) comprises connecting every one of the elements in the aperture to adjacent transducer elements of an array of transducer elements regardless of a position of the aperture relative to the transducer elements.

38. An ultrasound system for designating an aperture, the system comprising:
- a transmit beamformer comprising a plurality P of transmit channels M;
- a transducer comprising an array of at least 2P transducer elements numbered 1–2P sequentially from one end of a linear array to another end of the linear array; and
- a multiplexer for operatively connecting each one of said transmit channels M to the transducer elements numbered M and at least M+P, and to at least another transducer element selected from the group of: transducer element numbered M+1 and P+M−1, the multiplexer comprising less than 4P switches.

39. The system of claim 38 wherein the multiplexer is operative to connect each of the plurality of transmit channels to every second transducer element of a sub-set of the at least 2P transducer elements.

40. The system of claim 38 wherein the multiplexer is operative to connect at least one adjacent pair of the at least 2P transducer elements to a single one of the plurality of transmit channels.

41. The system of claim 40 wherein the at least one adjacent pair comprises adjacent pairs for each of the plurality P of the transmit channels.

42. The system of claim 38 wherein the transmit beamformer is operative to generate excitation waveforms at a fundamental transmit frequency further comprising:
- a receive beamformer operatively connected to the transducer; and
- a filter for obtaining ultrasound data at a harmonic of the fundamental transmit frequency.

43. The system of claim 38 wherein the multiplexer comprises 3P switches.

44. The system of claim 42 wherein the transducer transmits acoustic energy into a target during an imaging session, said target being free of ultrasound contrast agent throughout the entire imaging session.

45. The system of claim 38 wherein the transducer comprises 128 transducer elements.

46. The system of claim 38 wherein the multiplexer comprises a single layer of P switches operatively connected to the respective plurality P of transmit channels, each of the P switches operative to connect one of said transmit channels M to the transducer elements numbered M and at least M+P, and to at least another transducer element selected from the group of: transducer element numbered M+1 and P+M−1.

47. A method for designating an aperture in an ultrasound system, the method comprising the steps of:
(a) generating excitation waveforms with a transmit beamformer comprising a plurality P of transmit channels M;
(b) transmitting acoustic energy from a transducer comprising an array of at least 2P transducer elements numbered 1–2P sequentially from one end of a linear array to another end of the linear array; and
(c) connecting each one of said transmit channels M to the transducer elements numbered M and at least M+P, and to at least another transducer element selected from the group of: transducer element numbered M+1 and P+M−1 with a multiplexer, the multiplexer comprising less than 4P switches.

48. The method of claim 47 wherein step (c) comprises connecting each of the plurality of transmit channels to every second transducer element of a sub-set of the at least 2P transducer elements.

49. The method of claim 47 wherein step (c) comprises connecting at least one adjacent pair of the at least 2P transducer elements to a single one of the plurality of transmit channels.

50. The method of claim 47 wherein (b) comprises transmitting of a fundamental transmit frequency and further comprising:
(d) obtaining ultrasound data at the harmonic of a fundamental transmit frequency in response to step (b).

51. The method of claim 47 wherein step (c) comprises connecting with the multiplexer comprising 3P switches.

52. The method of claim 47 wherein step (b) comprises transmitting the acoustic energy into a target during an imaging session, said target being free of ultrasound contrast agent throughout the entire imaging session.

53. The system of claim 47 wherein step (c) comprises connecting with the multiplexer comprising a single layer of P switches operatively connected to the respective plurality P of transmit channels, each of the P switches operative to connect one of said transmit channels M to the transducer elements numbered M and at least M+P, and to at least another transducer element selected from the group of: transducer element numbered M+1 and P+M−1.

54. A method for obtaining ultrasound data during an imaging session with an ultrasound system, the method comprising the steps of:
(a) electrically connecting at least two adjacent transducer elements of an array of elements to a single transmit channel;
(b) generating an excitation waveform including a Gaussian envelope at a fundamental frequency with the single transmit channel;
(c) transmitting ultrasonic energy responsive to the excitation waveform from the at least two adjacent transducer elements; and
(d) obtaining ultrasound data at a harmonic of the fundamental frequency in response to step (c).

55. The method of claim 54 wherein step (a) comprises electrically connecting the at least two transducer elements with a multiplexer.

56. A method for obtaining ultrasound data during an imaging session with an ultrasound system, the method comprising the steps of:
(a) electrically connecting every other transducer element of a plurality of transducer elements to a respective number of channels;
(b) generating excitation waveforms at a fundamental frequency;
(c) transmitting ultrasonic energy responsive to the excitation waveform;
(d) receiving energy responsive to step (c); and
(e) obtaining ultrasound data at a harmonic of the fundamental frequency from the received energy;
wherein the connection of step (a) is used for performing both of steps (c) and (d).

* * * * *

UNITED STATES PATENT AND TRADEMARK OFFICE
CERTIFICATE OF CORRECTION

PATENT NO.    : 6,174,286 B1
DATED         : January 16, 2001
INVENTOR(S)   : Bhaskar S. Ramamurthy et al.

Page 1 of 1

It is certified that error appears in the above-identified patent and that said Letters Patent is hereby corrected as shown below:

<u>Title page,</u>
OTHER PUBLICATIONS, in the James B. Seward et al., reference insert -- a -- before "New".

<u>Column 12,</u>
Line 42, insert -- a -- before "sliding".

Signed and Sealed this

Twenty-eighth Day of May, 2002

Attest:

JAMES E. ROGAN
*Attesting Officer*    *Director of the United States Patent and Trademark Office*